United States Patent [19]

Buijs et al.

[11] Patent Number: 5,312,357
[45] Date of Patent: May 17, 1994

[54] CATHETER

[75] Inventors: Arnold Buijs; Michael W. C. M. Nieuwesteeg, both of Eindhoven, Netherlands

[73] Assignee: Drager Medical Electonic B.V., Best, Netherlands

[21] Appl. No.: 971,078

[22] Filed: Nov. 3, 1992

[30] Foreign Application Priority Data

Nov. 4, 1991 [EP] European Pat. Off. ......... 91202871.9

[51] Int. Cl.⁵ .............................................. A61M 25/00
[52] U.S. Cl. ..................................... 604/164; 604/170
[58] Field of Search ................... 604/164, 43, 44, 45, 604/170

[56] References Cited

U.S. PATENT DOCUMENTS

| Re. 27,297 | 10/1973 | Sorenson et al. ................. 4/162 |
| 2,118,631 | 5/1938 | Wappler ........................ 604/170 |
| 2,393,002 | 8/1948 | Smith . |
| 3,225,762 | 12/1965 | Guttman ........................ 604/164 |
| 3,499,435 | 3/1970 | Rockwell et al. . |
| 3,669,094 | 6/1972 | Heyer . |
| 4,114,603 | 9/1978 | Wilkinson . |
| 4,636,199 | 1/1987 | Victor ........................... 604/164 |
| 4,692,155 | 9/1987 | Zimmer . |
| 4,950,232 | 8/1990 | Ruzicka et al. . |
| 4,986,814 | 1/1991 | Burney et al. .................. 604/164 |
| 5,104,381 | 4/1992 | Gresl et al. ..................... 604/164 |
| 5,108,364 | 4/1992 | Takezawa et al. ............... 128/748 |

FOREIGN PATENT DOCUMENTS 1070179 6/1967 United Kingdom .
1187111 4/1970 United Kingdom .

OTHER PUBLICATIONS

PCT/US90/05804, Oct. 10, 1990, Hall et al.

*Primary Examiner*—Paul J. Hirsch
*Attorney, Agent, or Firm*—Bachman & LaPointe

[57] ABSTRACT

Catheter to be used in the skull area consisting of an elongated elastic tube having a closed distal end and having a connecting part arranged at the rear end. The tube comprises an opening at a predetermined distance from said distal end, the dimensions of said opening being sufficient for inserting an elongated manipulating needle into the tube such that the distal point of said needle contacts the closed distal top of the catheter. Furthermore the tube may comprise a closure element which is clamped around the tube and can be shifted along the tube between a first position in which said opening is covered by said closure element and at least one further position in which the opening is not obstructed.

10 Claims, 7 Drawing Sheets

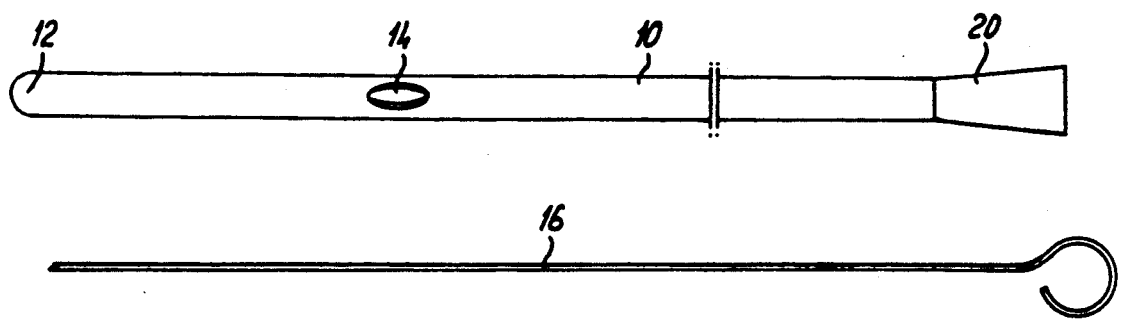
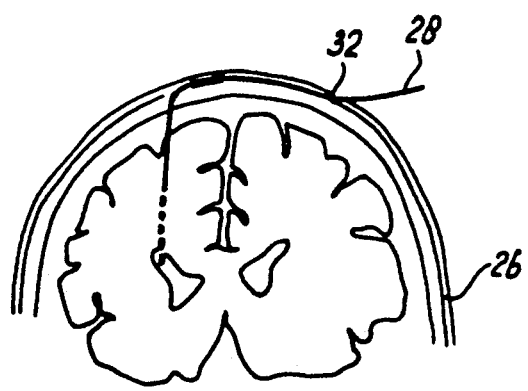

CATHETER

The invention relates to a catheter to be used in the skull area consisting of an elongated elastic tube having a closed distal end and having a connecting part arranged at the rear end.

Catheters of the above-mentioned type, especially to be used predominantly in the area of the skull in case of operations, are generally known. An example of such a catheter destined for measuring intracranial pressure, is for instance described in U.S. Pat. No. 3,669,094. The therein described catheter comprises an elongated drainage tube having a number of drainage openings near the distal tip of the tube and having connection means at the rear end to connect a pressure measuring device. The catheter, which is made from a relatively elastic and readily deformable material, is inserted into the cranium using an insertion rod which is shifted through the tubing until the distal end of the insertion rod meets the distal tip of the catheter. By means of this insertion rod the tubing is now inserted through a hole in the skull into the cranium, whereafter the insertion rod is at least partly removed to open the drainage holes near the distal portion of the catheter and to activate the pressure measuring means.

A serious problem with this type of prior art catheters is the possibility of infection. Whenever an incision is made through the scalp of a patient there is a possibility that an infection may occur at the locus of the incision. Accordingly, when a short direct tunnel through the scalp and skull is maintained over a period of monitoring, a path may be provided for the infection to migrate to the subdural space. Even more seriously, if the arachnoid membrane encasing the brain is penetrated, there is a possibility of infection within the brain itself.

This problem is recognized in U.S. Pat. No. 4,114,603. Therein an intracranial pressure monitoring catheter is presented which is installed using a subcutaneous tunnel between the scalp and the skull. To install the catheter a first incision is made in the scalp and an aperture is formed which penetrates the skull and dura meter, but not the arachnoid membrane. A second scalp incision, spaced apart from the first, is then opened and a subcutaneous tunnel is formed between the incisions. The catheter is then introduced through the second incision. passed through the subcutaneous tunnel and the aperture in the skull and is then inserted into the subdural space between the arachnoid membrane and dura meter. The incision above the skull hole is then closed and the proximal end of the catheter is attached to a suitable pressure measuring device. To remove the catheter at the conclusion of the monitoring period it is only necessary to pull on a portion of the catheter external to the scalp. Nothing, however, is said about the way in which the catheter is inserted in the meandering path formed by the subcutaneous tunnel, the hole through the skull and the area underneath the skull. Especially in case the catheter has to be used for measuring intracranial pressure as in U.S. Pat. No. 3,669,094 it will certainly be necessary to guide the catheter tip very carefully in a direction which can be almost perpendicular to the direction of the subcutaneous tunnel. A way to obtain a correct positioning of the catheter as a whole is described in U.S. Pat. No. 4,692,155.

The catheter tube described in U.S. Pat. No. 4,692,155 is longer than most known catheters. By means of an inserting needle, which is brought in the catheter from the rear end until the tip of the inserting needle abuts the distal end, the catheter is inserted in the skull and moved into the correct position. Thereafter the part extending outwards from the skull is partly cut off, a cannula is connected to the remaining end of the catheter and a separate tubing, which is passed through a subcutaneous tunnel between the scalp and the skull is connected to the other side of the cannula. Thereafter the incision above the hole in the skull is closed so that ultimately a situation comparable with the situation illustrated in FIG. 2 of U.S. Pat. No. 4,114,603 is obtained. The whole procedure of separately inserting the catheter in the skull and inserting the further tubing through the subcutaneous tunnel, cutting the catheter at the correct length after locating the catheter at the correct position, connecting the cannula to the catheter and connecting thereafter the further tubing to the cannula is considered very laborious and, because of the many parts involved, still has a certain risk on infection.

The object of the invention is now to provide a catheter which, in combination with an auxiliary manipulating needle or insertion rod can be inserted in the transcutaneous tunnel as well as through the hole in the skull and located at the correct position without having to cut the catheter and without having to use a separate cannula to connect the catheter to a further tubing, which runs through the transcutaneous tunnel.

This object of the invention is reached by a catheter which is characterized in that the tube comprises an opening at a predetermined distance from said distal end, the dimensions of said opening being sufficient for inserting an elongated manipulating needle into the tube such that the distal point of said needle contacts the closed distal top of the catheter and said predetermined distance being larger then the maximum length of the catheter to be introduced into the skull and shorter then the length of the manipulating needle. As will be explained in more detail with reference to the attached drawings a surgeon is able to shift the catheter through the subcutaneous tunnel using the manipulating needle, draw a sufficient length of the catheter tube through said tunnel, insert thereafter the distal end of the catheter into the skull again using the manipulating needle, withdraw the excess length of catheter tubing back through the subcutaneous tunnel and close the incision above the hole in the skull. It is thereby not necessary to cut the catheter tubing.

Dependent on the purpose of the catheter the hole in the catheter tube can be left open or has to be closed before the excess length of tubing is drawn back through the subcutaneous tunnel. If the opening has to be closed it is preferred that the catheter comprises a closure element which is clamped around the tube and can be shifted along the tube between a first position in which said opening is covered by said closure element and at least one further position in which the opening is free. In a specific embodiment the closure element consist of a short tube section fitting closely around the catheter tube such that the closure element can be moved between said aforementioned positions and such that the friction between the closure element and the catheter tube is sufficient to maintain the closure element in place during manipulation of the catheter, the length of said tube section being at least equal to the axial length of said opening.

To facilitate insertion of the manipulating needle into the catheter it is preferred that the opening in the tube has an elliptical shape whereby the longest dimension of the opening is parallel to the axis of the catheter tube.

If the catheter has to be applied for drainage purposes it is preferred that the catheter comprises near the distal end a number of passages rendering the catheter suitable for drainage purposes. However, if the catheter has to be used for measuring purposes it is preferred that the catheter carries at its distal tip a sensor for measuring a predetermined parameter of the space or matter in which the distal tip of the catheter is introduced whereby a communication line runs in general through the catheter tube from said sensor to the rear end of the catheter. Examples of parameters to be measured by a sensor on the distal tip of the catheter are pressure, oxygen content of blood or other fluid, glucose content of blood, temperature, pH-value of blood or other fluid, etc.

The invention will be explained in more detail with reference to the attached drawings.

FIG. 1a illustrates very schematical a basic embodiment of a catheter according to the invention.

FIG. 1b illustrates a cross-sectional view through a part of the catheter of FIG. 1a.

Figure 2A:
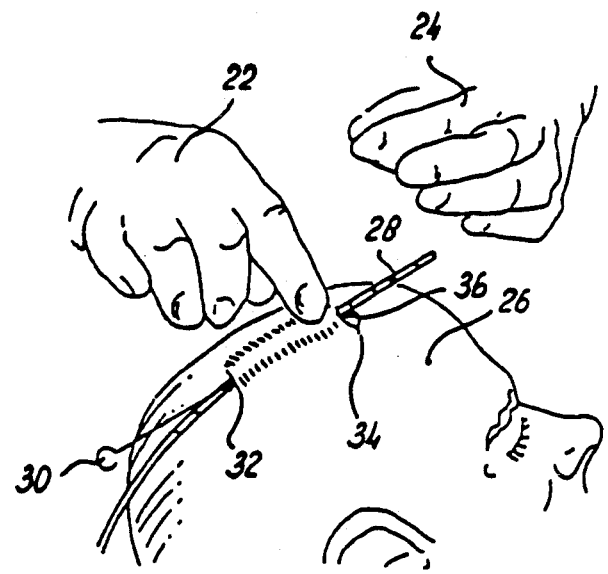

In FIGS. 2a... 2f the method of using the catheter under operative conditions is illustrative in more detail.

FIG. 3 shows a cross-sectional view through the head of a patient illustrating the ultimate position of the catheter within the skull of a patient.

Figure 4A:
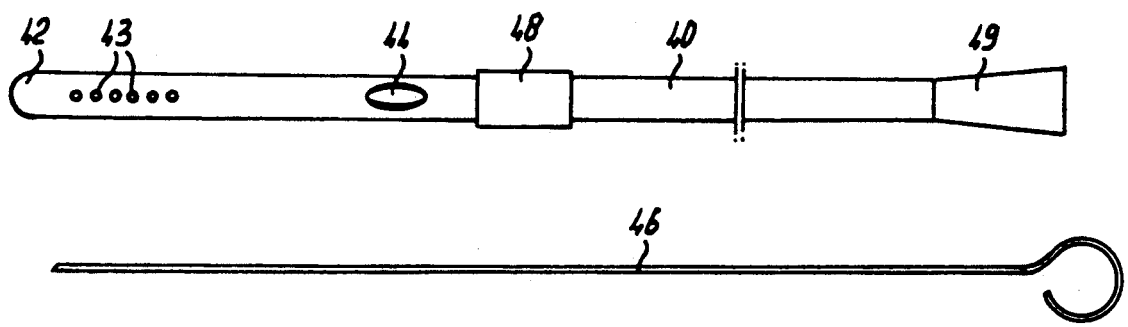
Figure 4B:
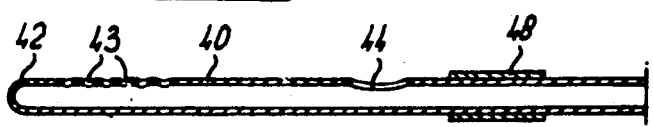

FIGS. 4a and 4b illustrate a further developed embodiment of a catheter according to the invention.

Figure 5A:
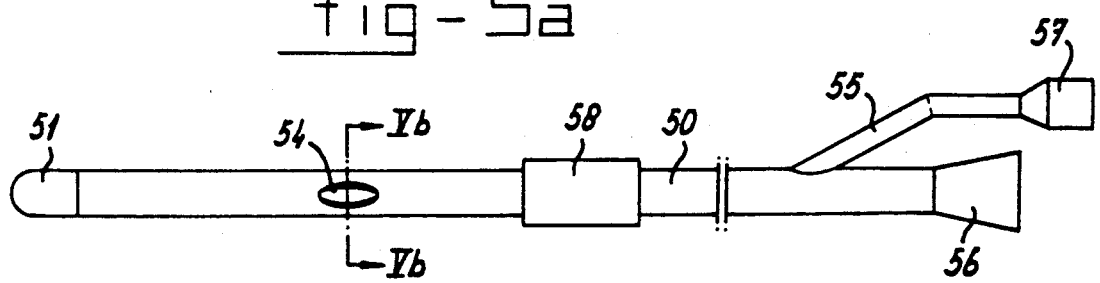
Figure 5B:
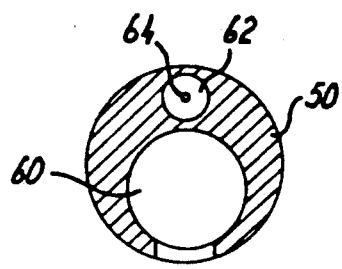

FIGS. 5a and 5b illustrate a another developed embodiment of a catheter according to the invention.

Figure 6A:
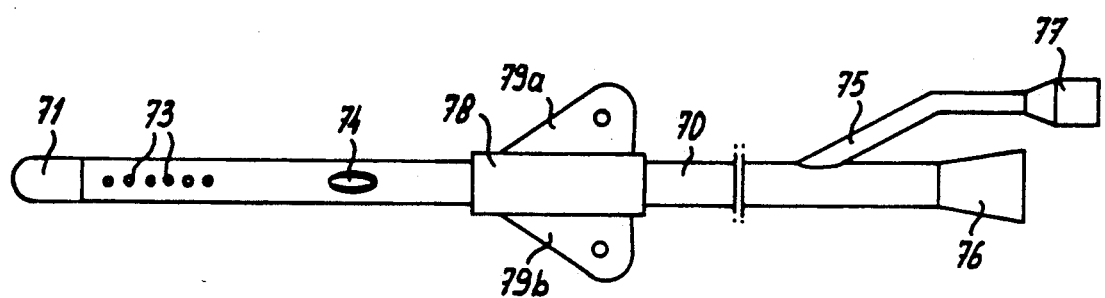
Figure 6B:
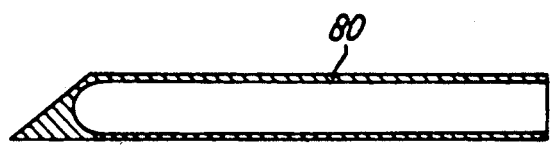

FIGS. 6a and 6b illustrate a still further embodiment of a catheter according to the invention.

Figure 7:
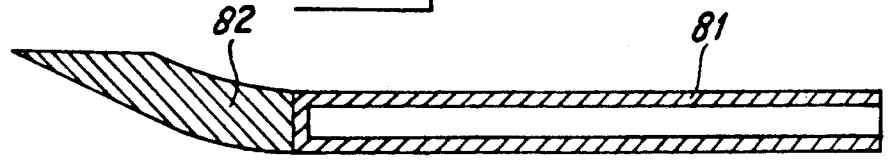

FIG. 7 illustrates a further embodiment of a catheter according to the invention.

In FIGS. 8a–8h a method of using the catheter generally illustrated in FIG. 4 is depicted.

FIG. 1a illustrates schematically a very basic embodiment of a catheter according to the invention. The catheter consists of an elongated length of tubing 10 of a flexible easily sterilizable material, for instance a medical rate plastics or silicon rubber. The distal end portion 12 of the catheter is closed. At a predetermined distance from this distal portion the catheter comprises an opening 14 of which the dimensions are sufficient to enable the insertion of an manipulating needle which in FIG. 1 is shown as the elongated needle 16. Preferably the opening 14 has an elliptical shape to facilitate the insertion of the manipulating needle 16. The way in which this needle is used will be described in more detail with reference to FIG. 2. The rear end 20 of the catheter is embodied such that the catheter can be connected to for instance a pressure monitoring device if the catheter is to be used for pressure measurements or to a drainage tube if the catheter is to be used for drainage purposes. More specifically the rear end may comprise a so called Luer lock.

It will be clear that if the catheter is used for drainage purposes the catheter should comprise a number of drain passages near the distal tip 12.

FIG. 1b illustrates a cross-sectional view through the catheter of FIG. 1a.

FIG. 2 illustrates in a series of perspective views, the way in which the catheter according to the invention can be used. The hands of the surgeon are schematically indicated by reference numbers 22 and 24. The skull of the patient is indicated by 26. It is remarked that for the sake of clearness the various reference numbers are not repeated in each of the FIGS. 2a... 2f.

For inserting the catheter first of all a pair of incisions 32 and 34 spaced a predetermined distance apart are made through the patient's scalp. A burr hole 36 is drilled through the skull at the site of one of the incisions 34 and a subcutaneous tunnel is formed between the first incision and the second incision underneath the scalp but above the skull. Thereafter the manipulating needle 30 is through the hole 14 inserted into the distal section of the catheter 28 and by means of this manipulating needle 30 the catheter 28 is shifted through the subcutaneous tunnel to obtain the situation which is illustrated in FIG. 2a.

Figure 2B:
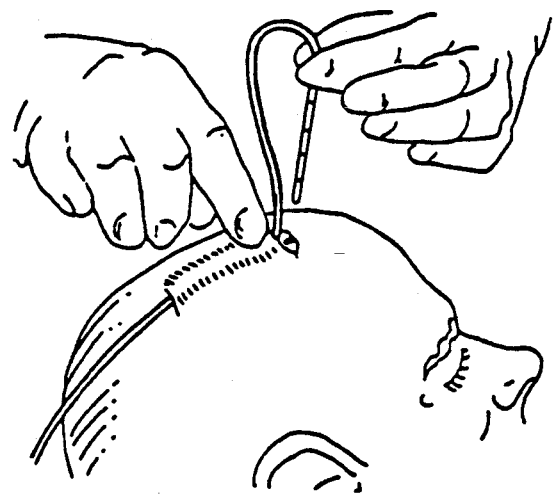

Thereafter the manipulating needle 30 is removed by withdrawing the needle, the catheter 28 is drawn further through the subcutaneous tunnel until a situation is obtained in which a sufficient length of the catheter tubing is passed the subcutaneous tunnel to make it possible for the surgeon to insert the distal end of the catheter into the hole 36 in the skull. The situation obtained is illustrated in FIG. 2b.

Figure 2C:
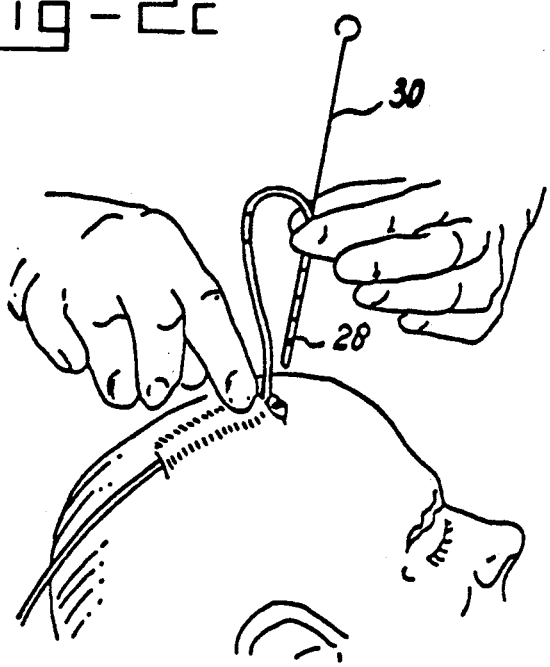
Figure 2D:
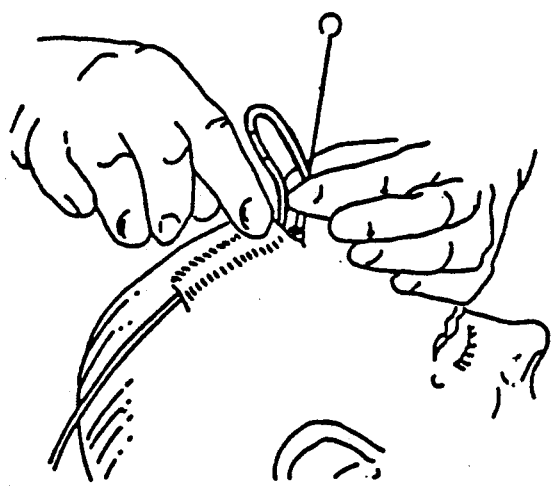
Figure 2E:
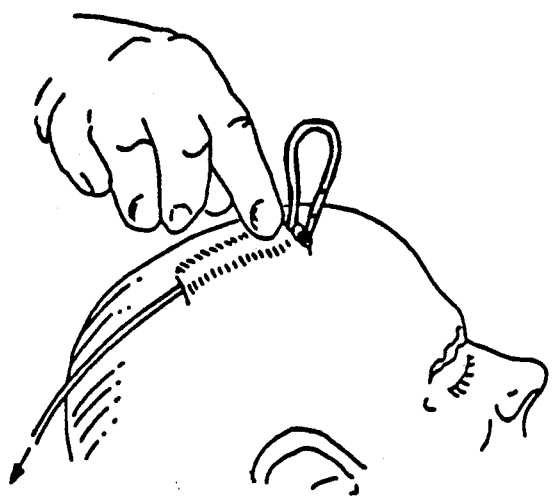

The surgeon inserts the manipulating needle 30 again through the hole 14 in the distal end of the catheter 28 as illustrated in FIG. 2c and thereafter starts the operation of inserting the catheter through the hole 36 in the skull into the brain region of the patient 26 as illustrated in FIG. 2d.

As soon as the catheter is inserted far enough through the burr hole 36 the inserting needle 30, which was used during the insertion process, is removed. By pulling at the rear end of the catheter tubing, as is symbolised by the arrow 31 in FIG. 2e, the tubing is pulled back so that the tubing slack between the end of the subcutaneous tunnel and the burr hole 36 will disappear resulting in a situation as illustrated in FIG. 2f.

Figure 2F:
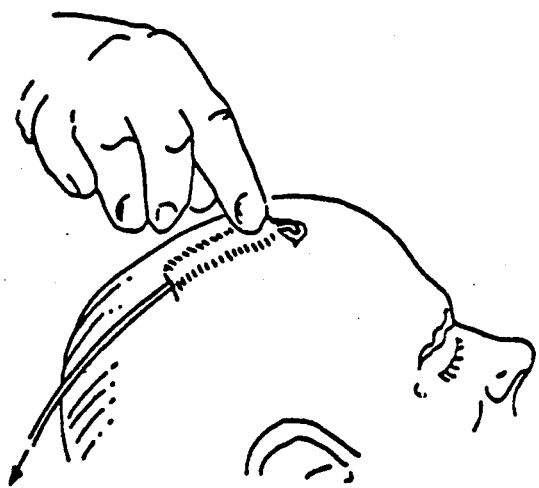

After reaching the situation illustrated in FIG. 2f the first incision 34 is closed and if necessary the tubing coming out from the subcutaneous tunnel at the other incision 32 is secured to the scalp of the patient by sutures.

FIG. 3 illustrates in cross-sectional view the way in which the catheter runs 28 from the first incision 38 through the subcutaneous tunnel into the brain area.

FIG. 4a illustrates a further development of a catheter according to the invention. The catheter consists of an elongated length of tubing 40 of a flexible easily sterilizable material, for instance a medical rate plastics or silicon rubber. The distal end portion 42 of the catheter is closed. At a predetermined distance from this distal end portion the catheter comprises an opening 44 of which the dimensions are sufficient to enable the insertion of an manipulating needle which in FIG. 4a is shown as the elongated needle 46. Preferably the opening 44 has an elliptical shape to facilitate the insertion of the manipulating needle 46. Near the distal tip the catheter comprises a number of drainage passages 43 which can be arranged in the wall of the catheter tube in any convenient pattern. The catheter comprises furthermore a closure element 48 in the form of a short tube section which is shiftable along the tubing 40 between a position in which the closure element completely closes the opening 44 and at least another position, which is for instance shown in FIG. 4a, in which the opening 44 is free. The rear end 49 of the catheter is embodied such that the catheter can be connected to for instance a pressure monitoring device if the catheter is to be used for pressure measurements or to a drainage tube if the catheter is to be used for drainage purposes.

FIG. 4b illustrates a cross-sectional view through the catheter of FIG. 4a. As already remarked the closure element 48 is preferably embodied as a short tube section which fits closely around the tubular catheter 40 such that on the one hand the element 48 is movable between a position in which the hole 44 is open such as illustrated in FIG. 4b and a position in which the hole 44 is covered completely by the closure element 48, whereas on the other hand the friction between the element 48 and the tube 40 is sufficient to maintain the element 48 in place during the manipulation of the catheter.

The manner in which the catheter according to FIGS. 4a and 4b is used is in general the same as described with reference to FIGS. 2a... 2f. The difference is that between the step illustrated in FIG. 2d and the succeeding step illustrated in FIG. 2e the closure element 48 is moved from the position in which the opening 44 is not obstructed to a position in which said opening is completely closed.

It is possible to use the embodiment of the catheter illustrated in FIG. 1 and to close the opening 14 at the appropriate stage of the operation using a piece of plaster or tape but the application of a closure element as illustrated in FIG. 4 is preferred because it eases the handling of the catheter and provides better conditions for maintaining the catheter sterile.

FIG. 5a illustrates a another development of a catheter according to the invention. Also in this embodiment the catheter consists of an elongated length of tubing 50 of a flexible easily sterilizable material, for instance a medical rate plastics or silicon rubber. The distal end portion of the catheter is closed and carries a transducer 51 for sensing a specific parameter of the space or matter in which the distal tip of the catheter will be introduced during usage. Examples of parameters to be measured by this sensor on the distal tip of the catheter are pressure, oxygen content of blood or other fluid, glucose content of blood, temperature, pH-value of blood or other fluid, etc.. A communication line runs in general through the catheter tube from said sensor to the rear end of the catheter in a manner which will be described with reference to FIG. 5b. At a predetermined distance from this distal end portion the catheter comprises an opening 54 destined to insert an manipulating needle which is not shown separately in this figure. The catheter comprises furthermore a closure element 58 in the form of a short tube section which is shiftable along the tubing 50 in the manner described already above with reference to FIGS. 4a and 4b. The rear end of the catheter is in this embodied bifurcated and comprises a conventional Luer cone 56 and comprises furthermore a connector 57 for connecting the communication line from the transducer 51 to an external measuring or recording apparatus.

FIG. 5b illustrates a cross-sectional view through the catheter of FIG. 5a in the direction of the arrows Vb—Vb in FIG. 5a. As appears from FIG. 5b the catheter has a main passage 60 running through the tube from the closed distal end to the Luer cone 56 at the rear end and has furthermore an auxiliary passage 62 for accommodating the already mentioned communication line running from the transducer 51 at the distal tip of the catheter through the branch tube 55 to the connector 57. In case the transducer supplies electrical signals the communication line 64 may comprise a number of metal wires. However, sensors are known which provide optical signals and in that case the communication line 64 comprises one or more optical fibers.

The use of a separate channel for guiding the communication line offers the advantage that the risk of damaging the communication line by the manipulating needle is eliminated.

A more sophisticated embodiment of the catheter is illustrated in FIG. 6a. As in the aforementioned embodiments the catheter consists of an elongated length of tubing 70 of which the closed distal end portion carries a transducer 71 for sensing a specific parameter of the space or matter in which the distal tip of the catheter will be introduced during usage. At a predetermined distance from this distal end portion the catheter comprises an opening 74 destined to insert an manipulating needle which in is not shown separately in this figure. The catheter comprises furthermore a closure element 78 in the form of a short tube section which is shiftable along the tubing 70 in the manner described already above with reference to FIGS. 4a and 4b. This closure element carries two fastening ears by means of which the closure element 78 can be fixed to the skull or skin of the patient in a known manner. The rear end of the catheter is in this embodied bifurcated and comprises a conventional Luer cone 76 and comprises furthermore a connector 77 for connecting the communication line, running in the above described manner through the catheter, to an external measuring or recording apparatus. The catheter has furthermore a number of drainage passages 73.

Preferably the catheter is inserted through the transcutaneous tunnel (method steps illustrated in FIG. 2a) in combination with a protective tubular shield 80 of which an example is illustrated in FIG. 6b. The inner diameter of the tubular shielding element is approximately equal to the outer diameter of the catheter tube 70 so that the distal end of the catheter 70 can be inserted into the shielding element 80 until the distal tip of the catheter abuts the distal end of the shielding element. The external shape of the distal end of element 80 is selected to facilitate the insertion of the element 80 together with the catheter 70 through the subcutaneous tunnel. The shielding element 80 is preferably made of stainless steel and preferably has a length at least equal to the length of the subcutaneous tunnel so that this element 80 can be used in stead of the manipulating needle. As soon as the catheter has passed the subcutaneous tunnel (situation illustrated in FIG. 2b) the shielding element is removed and the further operation is carried out as described with reference to FIGS. 2c... 2f. The advantage of using the shielding element 80 resides in the fact that the distal section is completely protected and is still sterile in the situation according to FIG. 2b.

Another embodiment of a tubular shielding element is illustrated in FIG. 7. This shielding element comprises a tubular section 81 of which the inner diameter is approximately equal to the outer diameter of the catheter tube to be used in combination with this shielding element. Furthermore the shielding element comprises a trocar point 82 which is slightly bended so is shown in FIG. 7. The way in which this bended tubular shielding element is used during a surgical operation is illustrated in FIG. 8.

FIG. 8 illustrates the use of a catheter which has in general the shape as illustrated in FIG. 4. At the start of the surgical operation the distal section of the catheter is inserted in the hollow tubular section of the shielding element as is illustrated schematically in FIG. 8a. In FIG. 8a the shielding element has reference number 90 and the catheter is indicated by 91. Furthermore a pair of incisions 92 and 94, spaced a predetermined distance apart, are made through the patient's scalp 93. A burr hole 96 is drilled through the skull at the site of one of the incisions 94 and a subcutaneous tunnel is formed between the first incision and the second incision underneath the scalp but above the skull. Thereafter the shielding element 90 with the therein inserted catheter 91 is shifted through the subcutaneous tunnel to obtain the situation which is illustrated in FIG. 8b.

Figure 8A:
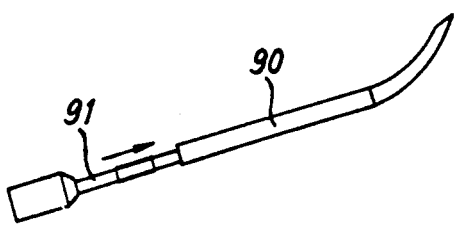
Figure 8B:
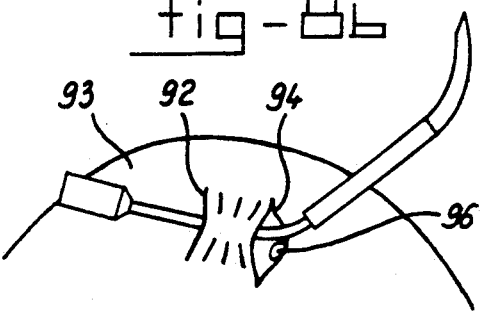
Figure 8C:
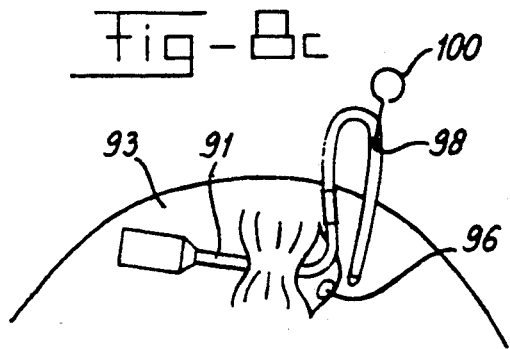
Figure 8D:
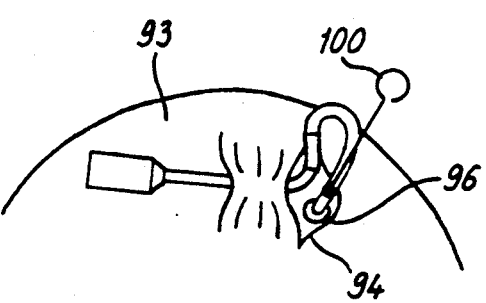

Thereafter the shielding element 90 is removed from the distal section of the catheter and a manipulating needle 100 is inserted through the hole 98 into the distal section of the catheter 91 as is illustrated in FIG. 8c. Thereafter the surgeon starts inserting the catheter through the hole 96 in the skull 93 into the brain region of the patient as illustrated in FIG. 8d.

Figure 8E:
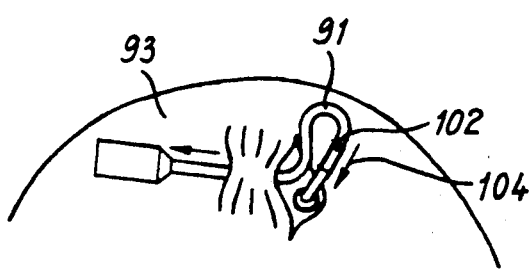
Figure 8F:
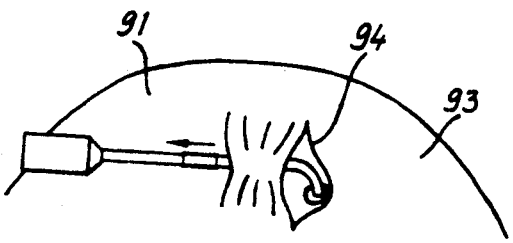

As soon as the catheter 91 is inserted far enough through the burr hole 96, the inserting needle 100, which was used during the insertion process, is removed and the hole 98 is closed by shifting the closing sleeve 102 over the hole 98 as schematically indicated by the arrow 104 in FIG. 8e. Thereafter the tubing is pulled back so that the tubing slack between the end of the subcutaneous tunnel and the burr hole 96 will disappear resulting in a situation as illustrated in FIG. 8f. As will be clear from this figure the position of the hole 98 is selected such that the part of the tubing wherein the hole is made is pulled back to a position outside the subcutaneous tunnel.

Figure 8G:
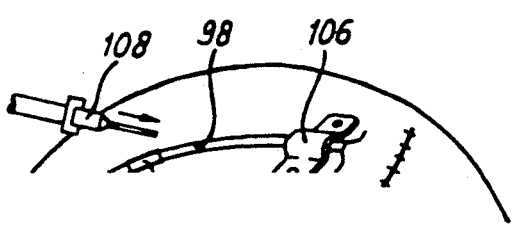

Thereafter the first incision 94 is closed and if necessary the tubing coming out from the subcutaneous tunnel at the other incision 92 is secured to the scalp of the patient for instance by means of a fixing clip 106, which schematically is indicated in FIG. 8g.

Figure 8H:
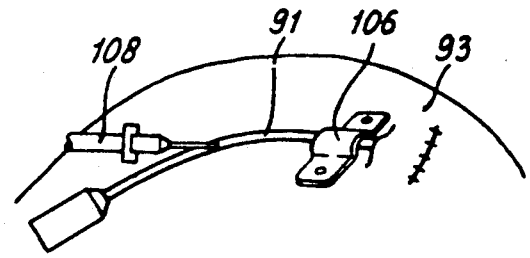

For some applications the procedure has now come to an end. However in other applications it is conceivable to use the hole 98 for connecting for instance a drainage tube to the catheter as is illustrated in FIG. 8g and 8h. The drainage tube in both figures is indicated by 108. As is shown in FIG. 8g and 8h first of all the hole 98 is opened by shifting the sleeve 104 over a sufficient distance. Thereafter the distal section of the drainage tube 108 is shifted through the hole 98 into the catheter 91. It will be clear that the shape of the distal section of the drainage tube 108 is adapted to the shape and dimensions of the hole 98 and to the inner diameter of the lumen of the catheter in which the drainage tube is inserted. By proper shaping and proper dimensioning and by a proper selection of materials a fluid tight connection can be realized between the drainage tube 108 and the catheter 91 in this manner.

We claim:

1. Catheter to be used in the skull area consisting of an elongated tube having a closed distal end and having a connecting part arranged at a rear end, said catheter characterized in that the tube has an opening at a predetermined distance from said distal end, said opening having dimensions sufficient for allowing insertion of an elongated manipulating needle into the tube such that a distal point of said needle contacts the closed distal end of the catheter, said needle having a desired length and being used to locate said catheter in said skull, said needle being removed through said opening after said catheter is located, and said predetermined distance being larger than a maximum length of the catheter introduced into the skull and shorter than the length of the manipulating needle.

2. Catheter according to claim 1, characterized in that the catheter comprises a closure element clamped around an exterior surface of the tube, said closure element being shiftable along the tube between a first position in which said opening is covered by said closure element and at least one further position in which the opening is not obstructed.

3. Catheter according to claim 2, characterized in that the closure element consists of a short tube section fitting closely around the catheter tube such that the closure element can be moved between said aforementioned positions and such that friction between the closure element and the catheter tube is sufficient to maintain the closure element in place during the manipulation of the catheter, said tube section having a length which is at least equal to an axial length of said opening.

4. Catheter according to claim 1, characterized in that the opening in the tube has an elliptical shape, and the longest dimension of the opening is parallel to the axis of a longitudinal catheter tube.

5. Catheter according to claim 1, characterized in that the catheter comprises a number of passages located near the distal end, said passages rendering the catheter suitable for drainage purposes.

6. Catheter according to claim 1, characterized by a sensor positioned at the distal end of said catheter for measuring a predetermined parameter of the space or matter in which the distal end of the catheter is introduced and by a communication line running through the catheter tube from said sensor to the rear end of the catheter.

7. Catheter according to claim 6, characterized in that at least a section of the communication line runs through a longitudinal channel in a wall of the catheter, said channel being separate from an inner space in which the manipulating needle is inserted.

8. Catheter according to claim 6, characterized in that said section of the communication line is embedded in the wall of the catheter tube.

9. Catheter according to claim 1, characterised in that the catheter is used in combination with a tubular shielding device which fits closely around the distal end of the catheter and which maintains the sterility of the respective distal end of the catheter.

10. Catheter according to claim 1 wherein said opening is located between said closed distal end and said rear end of the catheter.

* * * * *